US012805766B2

(12) United States Patent
Zvikhachevskaya et al.

(10) Patent No.: US 12,805,766 B2
(45) Date of Patent: Nov. 24, 2026

(54) DATA FUSION METHOD TO IMPROVE ACCURACY OF ALGORITHMIC PERFORMANCE IN MULTISENSORY DEVICES

(71) Applicant: Analog Devices International Unlimited Company, Limerick (IE)

(72) Inventors: Anna Zvikhachevskaya, Hertford (GB); Julie Byard, Huntingdon (GB)

(73) Assignee: Analog Devices International Unlimited Company, Limerick (IE)

(*) Notice: Subject to any disclaimer, the term of this patent is extended or adjusted under 35 U.S.C. 154(b) by 451 days.

(21) Appl. No.: 18/485,138

(22) Filed: Oct. 11, 2023

(65) Prior Publication Data

US 2025/0120615 A1 Apr. 17, 2025

(51) Int. Cl.
*A61B 5/145* (2006.01)

(52) U.S. Cl.
CPC ...... *A61B 5/14532* (2013.01); *A61B 5/14535* (2013.01)

(58) Field of Classification Search
CPC ............ A61B 5/14532; A61B 5/14535; G01N 27/3274; G01N 33/4915; G01N 33/4925; G01N 33/492
See application file for complete search history.

(56) References Cited

U.S. PATENT DOCUMENTS

| | | | |
|---|---|---|---|
| 2003/0235817 A1 | 12/2003 | Bartkowiak et al. | |
| 2005/0143635 A1* | 6/2005 | Kamath ............ | A61B 5/14532 600/347 |
| 2010/0292932 A1 | 11/2010 | Won | |

OTHER PUBLICATIONS

Shin et al., "A Correction Method Using a Support Vector Machine to Minimize Hematocrit Interference in Blood Glucose Measurements", Computers in Biology and Medicine, vol. 52, Jul. 2014, pp. 111-118.

Extended European Search Report issued in corresponding European Application No. 24 20 4888 dated Feb. 6, 2025.

* cited by examiner

*Primary Examiner* — Abid A Mustansir
(74) *Attorney, Agent, or Firm* — ArentFox Schiff LLP

(57) ABSTRACT

A multisensory device includes two or more sensors in contact with a channel, each sensor configured to output a corresponding level of an analyte in a sample in the channel. The multisensory device includes an analyzer having a memory and one or more processors. The analyzer is configured to receive a first input signal from a first sensor indicating a level of a first analyte and receive a second input signal from a second sensor indicating a level of a second analyte. The analyzer estimates the level of the second analyte based on a trace of the first input signal. The analyzer determines whether the level of the second analyte measured by the second sensor is comparable to the estimated level of the second analyte. The analyzer outputs an indication of the level of each of the first analyte and the second analyte.

20 Claims, 6 Drawing Sheets

DATA FUSION METHOD TO IMPROVE ACCURACY OF ALGORITHMIC PERFORMANCE IN MULTISENSORY DEVICES

TECHNICAL FIELD OF THE DISCLOSURE

The present disclosure relates generally to electrochemical sensors and, more specifically, to reference electrodes of electrochemical sensors.

BACKGROUND

Electrochemical sensors are a class of chemical sensors in which an electrode is used as a transducer element in the presence of an analyte. An electrochemical sensor may convert information associated with electrochemical reactions (e.g., the reaction between an electrode and an analyte) into an applicable qualitative or quantitative signal. Electrochemical sensors can produce electronic outputs in digital signals for further analysis.

A multisensory device may include multiple electrochemical sensors. In some cases, the presence of different analytes and/or the other sensors may be treated as noise or interference in the signal for an analyte.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In some aspects, the techniques described herein relate to a method of analyzing a sample, including: receiving measurements from two or more sensors in contact with a solution including two or more analytes, wherein each of the two or more sensors is configured to output a level of a corresponding analyte; determining, based on a trace of the level of a first analyte, whether a measurement of the first analyte is limited due to a level of a second analyte; estimating a level of the second analyte based on whether the measurement of the first analyte is limited; determining whether the level of the second analyte measured by a second sensor is comparable to the estimated level of the second analyte; and outputting an indication of the level of each of the first analyte and the second analyte.

In some aspects, the techniques described herein relate to a multisensory device, including: two or more sensors in contact with a channel, each sensor configured to output a corresponding level of an analyte in a sample in the channel; a memory storing computer-executable instructions; and one or more processors, individually or in combination, configured to: receive a first input signal from a first sensor of the two or more sensors indicating a level of a first analyte; receive a second input signal from a second sensor of the two or more sensors indicating a level of a second analyte; estimate the level of the second analyte based on a trace of the first input signal; and determine whether the level of the second analyte measured by the second sensor is comparable to the estimated level of the second analyte; and output an indication of the level of each of the first analyte and the second analyte.

To the accomplishment of the foregoing and related ends, the one or more aspects comprise the features hereinafter fully described and particularly pointed out in the claims. The following description and the annexed drawings set forth in detail certain illustrative

BRIEF DESCRIPTION OF THE DRAWINGS

To provide a more complete understanding of the present disclosure and features and advantages thereof, reference may be made to the following description, taken in conjunction with the accompanying figures, wherein like reference numerals represent like parts, in which.

DETAILED DESCRIPTION

Figure 1:
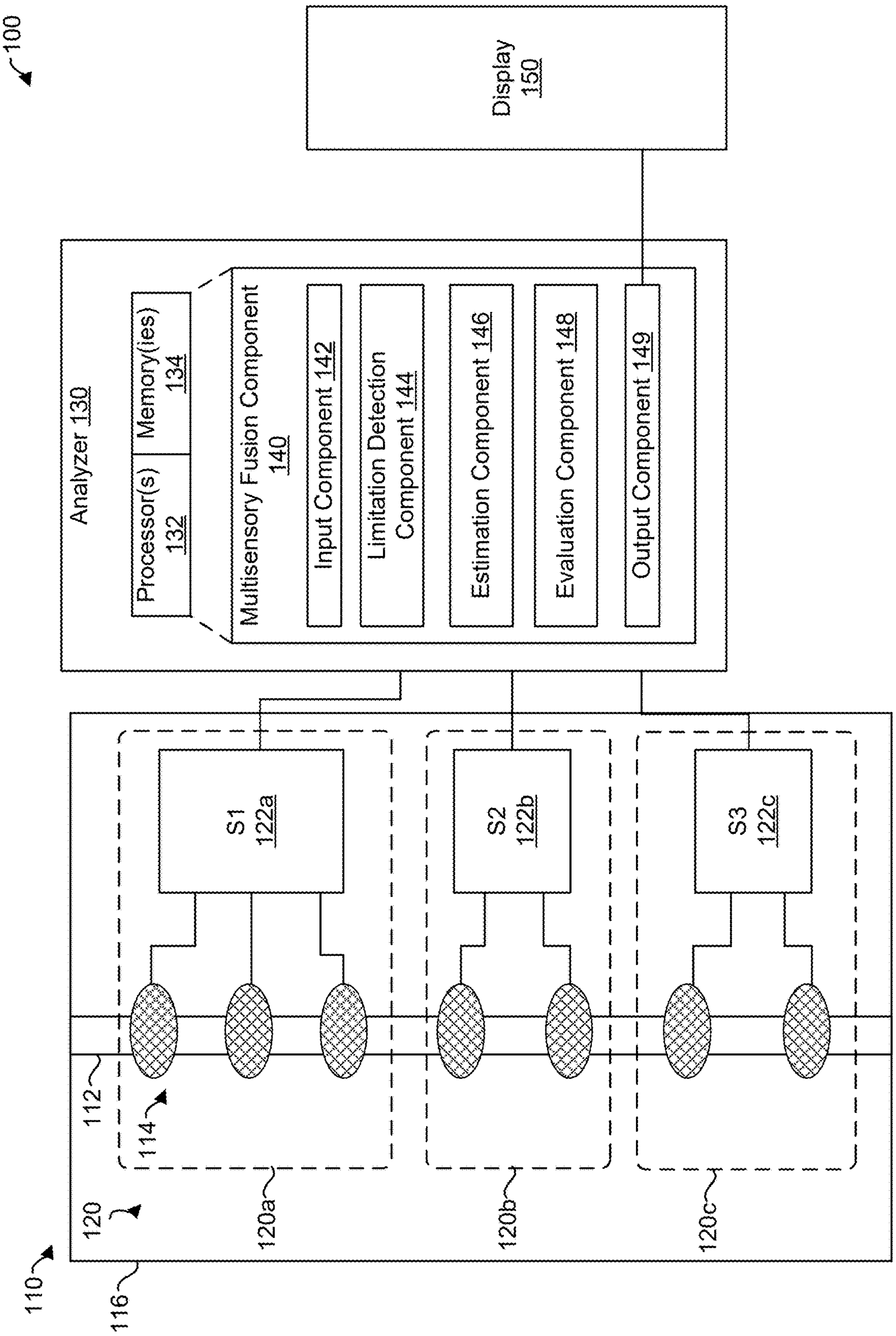
FIG. 1 is a diagram of an example multisensory device including electrochemical sensors according to an aspect of the present disclosure.

An electrochemical sensor has advantages such as simple measurement procedure, short response time, and sufficient sensitivity and selectivity. Electrochemical sensors have found widespread use in numerous applications. Biosensors are examples of such sensors. A biosensor is an analytical device that converts a biological response into an electrical signal.

An electrochemical sensor usually includes multiple types of electrodes in contact with an electrolyte. These electrodes may include working electrode (or sensing electrode), reference electrode, and counter electrode. A working electrode often includes two main components: a recognition element and a transducer. The recognition element selectively reacts with an analyte. This reaction is then converted into an electrical signal by the transducer. The recognition element and transducer form a sensing electrode of the electrochemical sensor. An electrochemical sensor may include multiple working electrodes. A reference electrode is usually held at a constant electrode potential with respect to the working electrode. In potentiometric sensors, the sensor response is a potential (voltage) differential that is measured between a sensing electrode (electrode where the chemical phenomena of interest takes place) and a reference electrode with stable reference potential that is not influenced by the analytes. The reference electrode serves as stable reference voltage for the measurement. In Amperometric (or Voltametric, etc.), the sensor response is a current that is measured between the sensing electrode and a counter electrode (in which counter reactions occur). Typically in Amperometric sensors (or Voltametric, etc.) a bias voltage is applied to the sensing electrode, in order to facilitate chemical reactions or physical processes. In the latter case, the bias voltage is applied against the reference electrode, so again it is important that the reference electrode potential is stable. Additionally, a presence of substances which interact with the working electrode/electrolyte interface can invoke current flow between the working electrode and the counter electrode as a result of reduction/oxidation (REDOX) reactions at the working electrode. In some cases, it can invoke a change in electrode potential, which is a result of the interaction between the analyte and the working electrode. In some other cases, it is a change in impedance or resistance, which may be proportional to the concentration of analyte.

A multisensory device has multiple sources of information (sensors). An example of a multisensory device is a blood gas analyzer (BGA), which may be a bedside unit for monitoring a patient in a hospital. A BGA may be always connected to the patient via an arterial line. The BGA may include an array of biosensor technology on a silicon chip. Each biosensor may be a miniaturized electrochemical sensor. The BGA may perform glucose analysis and other calculated parameters, such as P/F ratio and temperature corrected gases. For instance, a BGA may monitor levels of oxygen (O), hematocrit (HCT), and/or hemoglobin (HB) (The ability to monitor blood gases and measure blood glucose frequently and easily, directly by the patient, can enable earlier interventions and closer patient management. A BGA may include a medical grade tablet monitor with a touchscreen user interface. All results may be reported to the monitor and/or transferred directly into laboratory information systems and electronic patient records.

One issue faced by a multisensory device is the interactions between various analytes in a sample during a measurement by the various sensors of the multisensory device. These sensors at any given point in time are connected via solution (i.e., exposed to the same solution) but the electrochemistry within sensors is tailored to react to only one specific analyte. In some cases, the signal generated by a sensor for a specific analyte may be affected by a level of another analyte, which may result in a noisy or inaccurate reading. Conventionally, a device may be able to detect an issue with a reading and indicate that another reading is needed.

In an aspect, the present disclosure provides for data fusion methods to improve accuracy of algorithmic performance in multisensory devices. Based on observed relationships and effects of analyte levels and the electrochemistry of the various sensors in the multisensory device, a trace of a signal from a first sensor may be used to identify an effect on the electrochemistry of a second sensor or estimate a level of the analyte that is detected by the second sensor. For example, based on a trace of the level of a first analyte, a multisensory device may determine whether a measurement of the first analyte is limited due to a level of a second analyte. As another example, a level of a third analyte may be estimated based on a trace of a level of a first analyte as a sample is flushed from the sensor.

The multisensory device of present disclosure may provide for improvement in the accuracy and reliability of measurements of analytes. For example, confirming that a measurement of a dedicated sensor is comparable with an estimation based on another sensor may increase confidence in the measurement. In some cases, a disagreement of the measurement and an estimate may detect possible limits on the sensor technology. The multisensory device may warn of such limits.

Several aspects of a multisensory system will now be presented with reference to various apparatus and methods. These apparatus and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more example implementations, the functions described may be implemented in hardware, software, or any combination thereof. If implemented in software, the functions may be stored on or encoded as one or more instructions or code on a computer-readable medium. Computer-readable media includes computer storage media, which may be referred to as non-transitory computer-readable media. Non-transitory computer-readable media excludes transitory signals. Storage media may be any available media that can be accessed by a computer. By way of example, and not limitation, such computer-readable media can include a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

FIG. 1 is a diagram of an example multisensory system 100. The multisensory system 100 includes a multisensory device 110, an analyzer 130, and a display 150. For example, the multisensory system 100 may be a blood gas analyzer (BGA), including multiple electrochemical sensors 120 that each detect a level of a particular analyte. For example a first sensor 120*a* may be a glucose sensor, a second sensor 120*b* may be a hematocrit sensor, and a third sensor 120*c* may be an oxygen sensor. Each sensor 120 may generate a signal indicating the level of the respective analyte and output the signal to the analyzer. The analyzer 130 may perform operations to process the signals (e.g., average, categorize, etc.) to generate output for presentation on the display 150.

The multisensory device 110 may include a substrate 116 having a channel 112 formed therein. The substrate 116 may include a plastic material, a semiconductor material (e.g., silicon, glass, etc.), a ceramic material, other types of material, or some combination thereof. The substrate 116 may be fabricated using, for example, injection moulding, laminating, flexible/build up or additive manufacturing technologies, or other suitable techniques depending on the specific requirements of the application of the electrochemical sensor.

The channel 112 is configured to receive a sample of a solution containing a plurality of analytes. For example, in a BGA, the sample may be a blood solution. For instance, the multisensory system 100 may be connected to a line (not shown) from the patient from which a blood sample may be drawn. A base solution (e.g., water and electrolytes) may be coupled with the channel 112 to flush the sample. The multisensory device 110 may further include a pump (not shown) configured to move the solutions through the channel 112.

A plurality of electrodes 114 are in contact with the channel 112. For example, the electrodes 114 may include working electrodes, reference electrodes, or counter electrodes. The working electrodes include electrically conductive contacts (also referred to as "conductive contacts"). A conductive contact includes an electrically conductive material, which may be a metal, e.g., gold (Au), etc. In some embodiments, a conductive contact is recessed in the substrate 116. For instance, a working electrode may include a working well and a conductive contact over (e.g., underneath) an end of the working well. In other embodiments, a conductive contact may be inlaid or protruding. In some implementations, a group of electrodes, along with the channel 112 and solution therein form an ion-sensitive field-effect transistor (ISFET) that detects changes in chemical properties of the solution. The electrodes 114 are coupled to sensor circuitry 122 for controlling and reading the electrodes 114. A group of electrodes 114 and sensor circuitry 122 may form a sensor 120 for measuring a particular analyte. For instance, a first sensor 120*a* may include circuitry 122*a* for detecting a level of a first analyte, a second sensor 120*b* may include circuitry 122*b* for detecting a level of a second analyte, and a third sensor 120*c* may include circuitry 122*c* for detecting a level of a third analyte. Each of the sensors 120 outputs a signal indicating a level of the respective analyte.

In an implementation, the first sensor 120*a* is a glucose sensor. An example glucose sensor is an Amperometric sensor. Amperometry is based on the measurement of the current between the working and counter electrode which is induced by a redox reaction at the working electrode. The conditions are chosen in such a way that the current is directly proportional to the concentration of a redox active species in the analyte solution. In this case hydrogen peroxide. An electrolyte containing glucose oxidase enzyme is dispensed into the inner well of the amperometric sensor. The electrolyte is then covered with a suitable membrane. The membrane functions to stop the enzyme leeching out of the sensor, control the levels of glucose and oxygen entering the sensor and reduce any impact of fouling when the sensor is exposed to blood. The second sensor 120*b* may be an oxygen sensor. An example oxygen sensor is an amperometric sensor. Like the glucose sensor, it is a double ring structure with working, counter and reference electrodes. A salt based electrolyte is dispensed in the inner ring and a gas permeable membrane is dispensed over both ring structures. Oxygen permeates from the test solution into the electrolyte through a membrane and is converted to a current at the working electrode. The resulting current is proportional to the oxygen partial pressure in the test solution. The third sensor 120 may be a hematocrit sensor. An example hematocrit sensor is a conductometric sensor which includes three electrodes. One electrode is at the entrance of the sample flow path and one electrode is at the exit of the flow path. The last electrode is a pseudo-reference electrode. The conductivity technique is based on the principle that because plasma is more conductive than blood cells due to the high resistance of the cell membranes, the resistivity of blood will increase as the concentration of cells increases. In another example, an optical sensor may measure a hemoglobin (hb) level, which may also be indicative of a hematocrit level.

The analyzer 130 is configured to receive the signals from the sensors 120 and generate a display output with pertinent information to the display 150. For example, in the case of a BGA, the analyzer 130 may output levels of the analytes as well as warnings based on the levels and/or information about the accuracy or reliability of the levels of the analytes.

The analyzer 130 may include one or more processors 132 coupled to one or more memories 134. The memories 134 may store computer-executable instructions defining a multisensory fusion component 140 configured to analyze a signal from a sensor in view of one or more signals from other sensors. The processor 132 may execute the computer-executable instructions.

The multisensory fusion component 140 may include an input component 142, a limit detection component 144, an estimation component 146, an evaluation component 148 and an output component 149. The input component 142 is configured to receive measurements from two or more sensors in contact with a solution including two or more analytes. Each of the two or more sensors 120 is configured to output a level of a corresponding analyte. The limit detection component 144 is configured to determine, based on a trace of the level of a first analyte, whether a measurement of the first analyte is limited due to a level of a second analyte. The estimation component 146 is configured to estimate the level of the second analyte based on a trace of the first input signal. In some implementations, the estimation component 146 is also configured to estimate a level of the third analyte based on the trace of the level of the first analyte. The evaluation component 148 is configured to determine whether the level of the second analyte (or third analyte) measured by a respective sensor is comparable to the estimated level of the second analyte (or third analyte). The output component 149 is configured to output an indication of the level of each of the analytes.

The display 150 is configured to present the output of the analyzer 130. For example, the display 150 may be a computer monitor or touch screen display. The display 150 may present the most recently detected levels of the analytes. In some implementations, the display 150 includes a chart of historical levels of the analytes. The display 150 may also present information regarding the reliability of the levels of analytes. For instance, the display 150 may indicate whether a level of analyte was confirmed by a second sensor.

Figure 2:
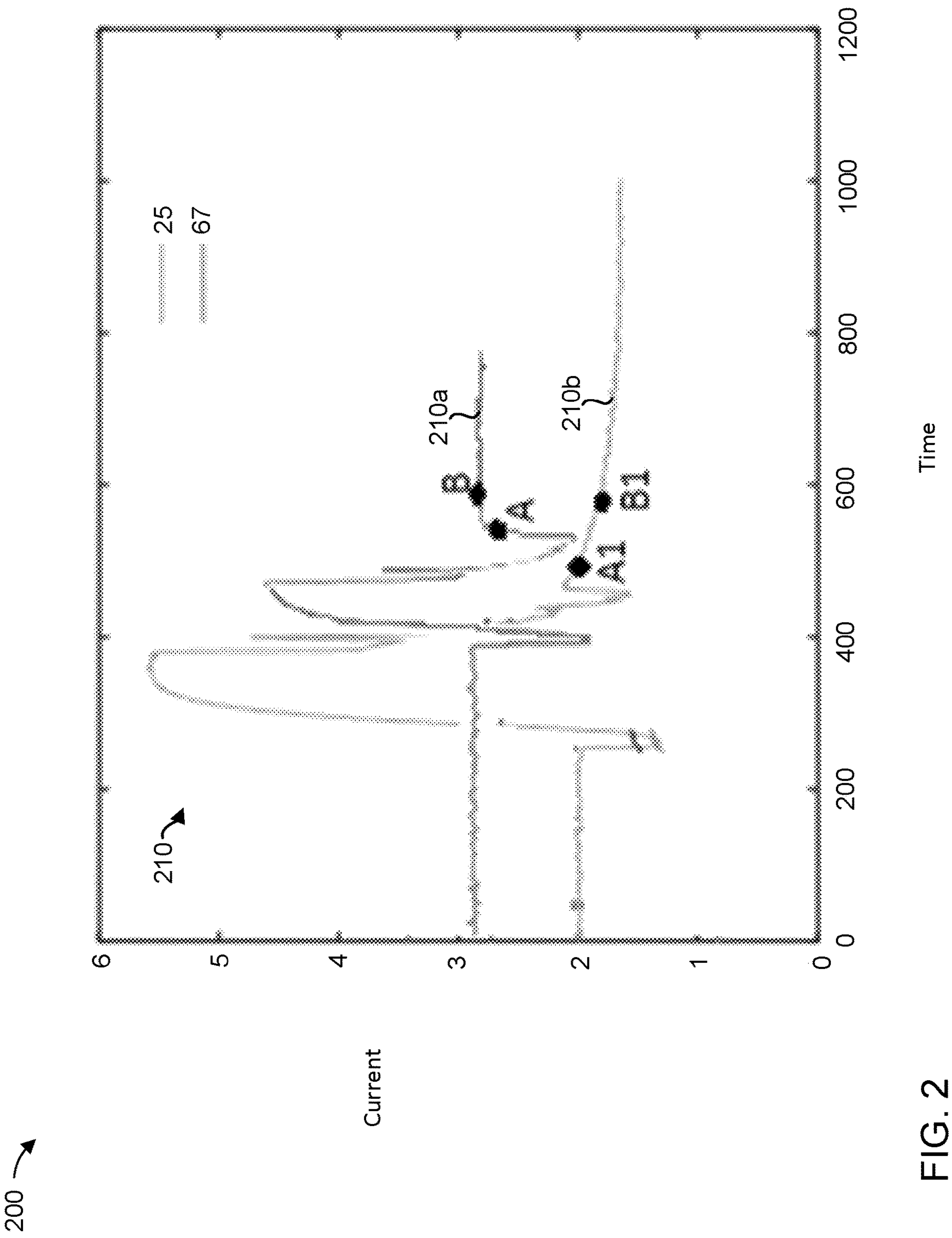
FIG. 2 is a graph of traces of a signal from a sensor according to an aspect of the present disclosure.

FIG. 2 is a graph 200 of traces 210 of a signal from a sensor 120. For example, for the illustrated traces 210, the sensor is a glucose sensor, which may be the first sensor 120*a*.

In an implementation, effects of a second analyte such as HCT may be read on a trace of the first analyte (e.g., glucose). In particular, low HCT levels impart noticeable shape changes on the glucose trace 210 when the HCT level is low. In contrast, normal and high HCT levels have no noticeable impact on the glucose trace. The effects of HCT levels may be due to a mixture effect when the sample is flushed from the channel 112. The level of HCT in a blood sample is related to the viscosity level in the blood. Hence, during the push back of the blood sample the trace for glucose will reflect the different levels of HCT due to the high/low viscosities of the samples. The signal from the glucose sensor 120*a* will have an indication of the pressure change and hence a change in the mixing effects due to the viscosity levels of blood associated with hematocrit.

In an aspect, an estimate of the level of HCT in a blood sample may be based on the trace 210 of the glucose level. In each trace 210, as the sample is present, the detected current rises, then the detected current falls as the sample is flushed from the channel 112. The current returns to a baseline level once the sample is flushed. In a first trace 210*a*, the baseline (B) measurement is greater than a measurement (A) during the sample. This condition indicates that the level of HCT is high. For instance, the low HCT results in a lower than normal viscosity allowing the sample to quickly clear and return to the baseline. In the second trace 210*b*, the baseline (B1) measurement is less than the measurement (A1) during the sample. This condition indicates that the level of HCT is low. For instance, the low level of HCT results in a higher viscosity such that the sample takes longer to clear and the current remains high, more slowly returning to the baseline. It is also possible that the measurement during the sample is approximately equal to the baseline, in which case the HCT level may be normal.

Figure 3:
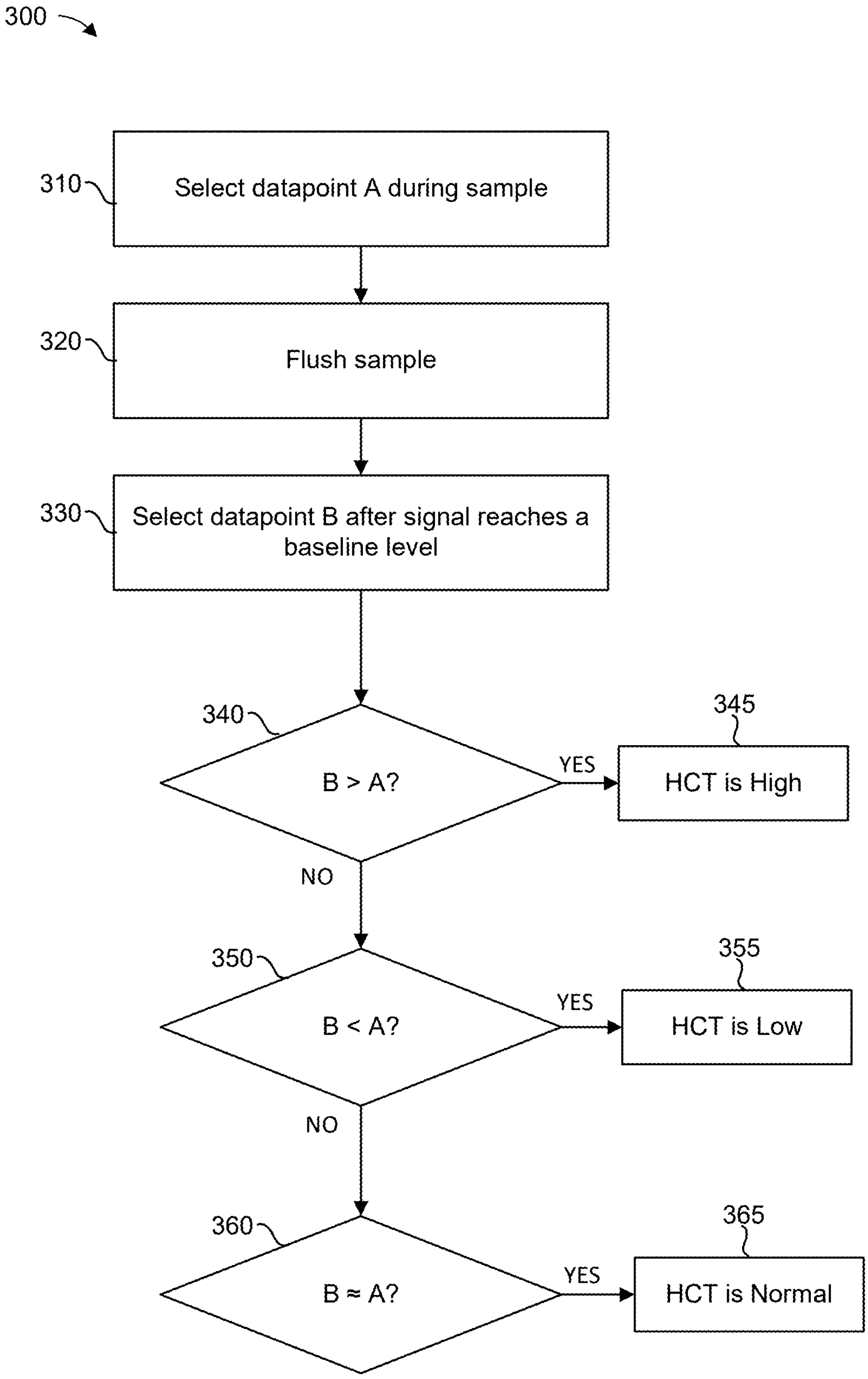
FIG. 3 is a logical flow diagram of a method of estimating a hematocrit (HCT) level based on trace of a glucose level according to an aspect of the present disclosure

FIG. 3 is a logical flow diagram of a method 300 of estimating a HCT level based on a trace 210 of a glucose level. The method 300 may be performed by the analyzer 130 executing the multisensory fusion component 140 and/or the estimation component 146. In block 310, the method 300 includes selecting a datapoint A during a sample. In some implementations, the measurement for datapoint A during the sample is taken when a flushing process is initiated or a change in pressure is detected, indicating a start of the flushing process. In block 320, the method 300 includes flushing the sample. For example, the channel 112 may be flushed with a base solution. In block 330, the method 300 includes selecting a datapoint B after the signal from the first sensor reaches a baseline level. In some implementations, the baseline (B) is read when the current remains constant for a threshold period of time.

In block 340, the method 300 includes evaluating whether the baseline (B) is greater than the measurement (A). In some implementations, a threshold may be used to detect a significant difference. For example, the block 340 may be true when the datapoint B is greater than the datapoint A by at least 0.1 milliamps (mA). A greater threshold may be used to ensure a more accurate result (e.g., fewer false positives). If block 340 is true, in block 345, the method 300 includes determining that the HCT level is high. In an implementation, a high HCT level may represent a range of possible HCT levels (e.g., above 50%).

In block 350, the method 300 includes evaluating whether the baseline (B) is less than the measurement (A). In some implementations, a threshold may be used to detect a significant different. For example, the block 350 may be true when the datapoint B is less than the datapoint A by at least 0.1 milliamps (mA). If block 350 is true, in block 355, the method 300 includes determining that the HCT level is low. In an implementation, a low HCT level may represent a range of possible HCT levels (e.g., between 15% and 40%).

In block 360, the method 300 includes evaluating whether the baseline (B) is substantially equal to the measurement (A). In some implementations, a threshold may be used to determine whether the baseline and measurement are substantially equal. For example, the block 350 may be true when the datapoint B is within the threshold (e.g., ±0.1 milliamps (mA)) of the datapoint A. If block 360 is true, in block 365, the method 300 includes determining that the HCT level is normal. In an implementation, a low HCT level may represent a range of possible HCT levels (e.g., 30%-65%).

Figure 4A:
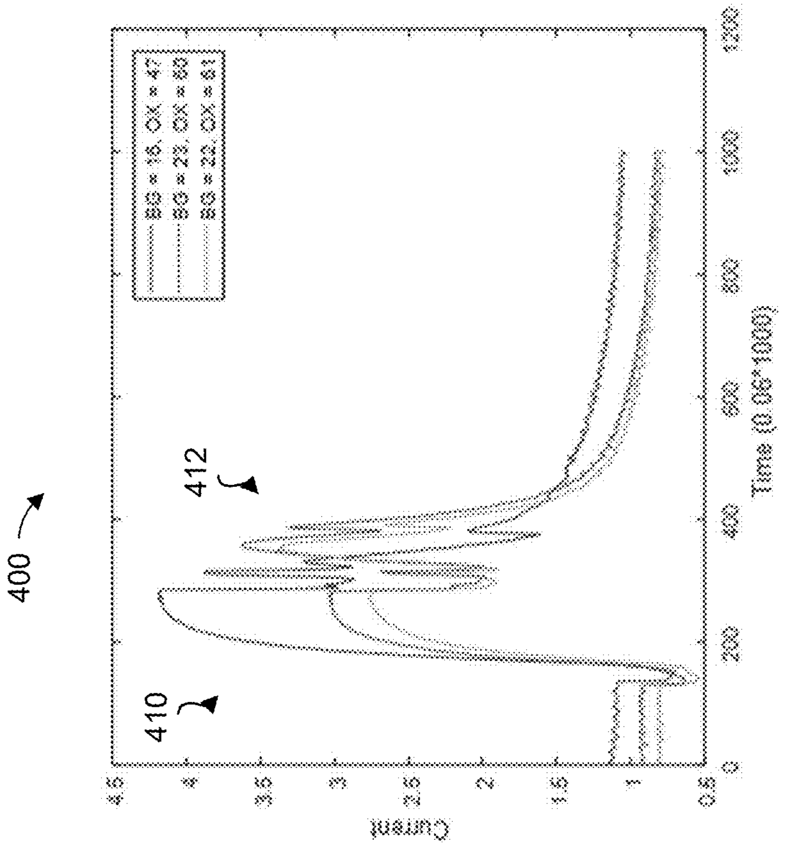
FIG. 4A is a graph of traces of a signal for a first analyte showing a limitation due a level of a second analyte according to an aspect of the present disclosure.
Figure 4B:
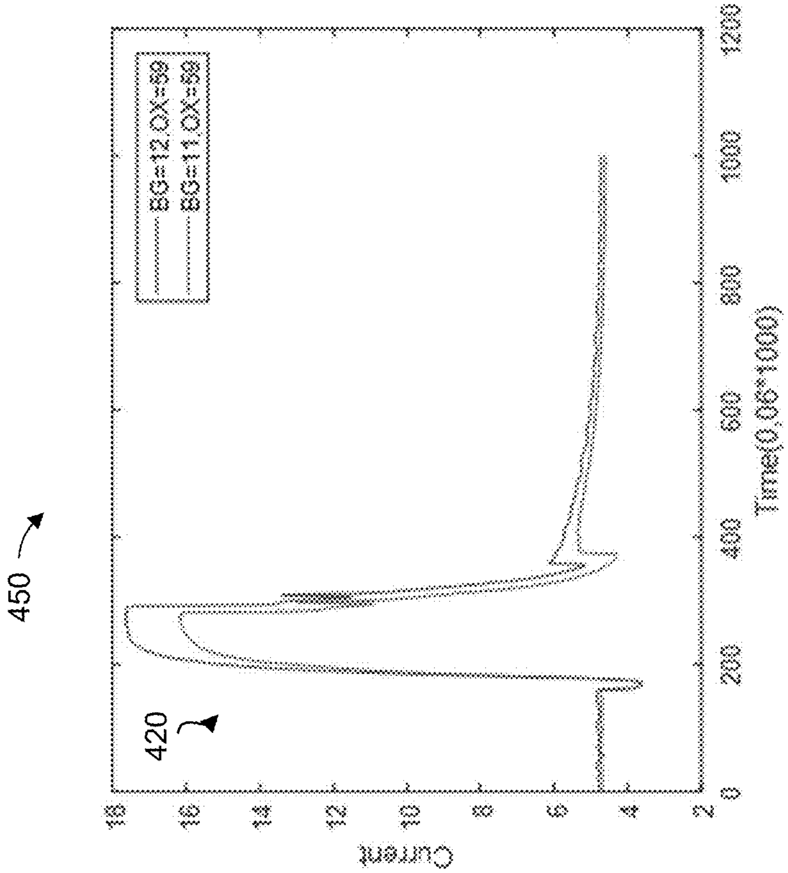
FIG. 4B is a graph of traces of the signal for the first analyte without the limitation due to the level of the second analyte according to an aspect of the present disclosure.

FIG. 4A is a graph 400 of traces 410 of a signal for a first analyte showing a limitation due a level of a second analyte. For example, for the illustrated traces 410, the sensor is a glucose sensor, which may be the first sensor 120*a*. In an implementation, a low oxygen level may affect the traces 410 of a glucose level. Oxygen limitation is an effect on the glucose trace. In order for the glucose oxidation reaction involved in measurement of glucose level to happen in a reliable manner, oxygen level in the blood should be as close to normal or higher. Hence, if the oxygen level is low, the glucose oxidation reaction may not occur regularly, resulting in a period 412 of high variance and volatility visible in the traces 410, which may limit the ability of a glucose sensor to detect FIG. 4B is a graph of traces 420 of the signal for the first analyte without the limitation due to the level of the second analyte. The traces 420 do not have the period 412 of high variance and volatility.

In some implementations, an oxygen limitation may cause a glucose sensor to display extremely wrong glucose levels. For instance, in order for the enzyme within a glucose sensor to react with glucose in blood, the glucose sensor needs oxygen. When oxygen in blood is low it causes the glucose sensor to malfunction. This can be seen in a high variance in the signal from the glucose sensor. The oxygen level may also be monitored by a separate oxygen sensor. If both (signal change within glucose sensor suggests low oxygen and the oxygen sensor signal) then oxygen limitation is evident. In such cases the multisensory system 100 may warn a user of the limitations of the sensor technology. Furthermore, when an oxygen limitation check is triggered and oxygen level is low, the multisensory system 100 may generate an alarm for the user because oxygen levels are critical.

Figure 5:
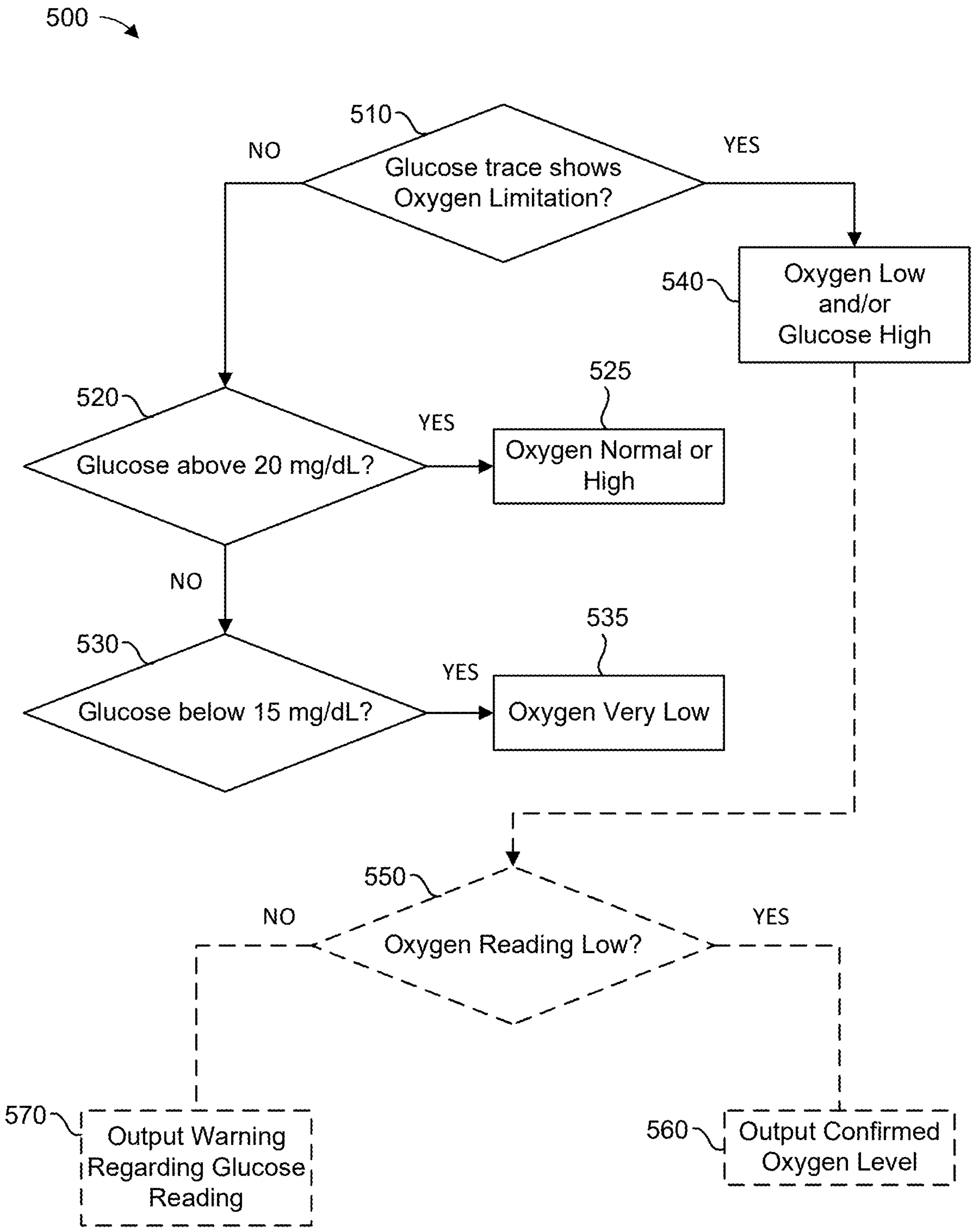
FIG. 5 is a logical flow diagram of a method of estimating an oxygen level based on trace of a glucose level according to an aspect of the present disclosure.

FIG. 5 is a logical flow diagram of a method 500 of estimating an oxygen level based on trace of a glucose level. The method 500 may be performed by the analyzer 130 executing the multisensory fusion component 140 and/or the estimation component 146.

In block 510, the method 500 includes determining whether the glucose trace shows an oxygen limitation. For example, the limit detection component 144 may detect an oxygen limitation based on the trace 410. The limit detection component 144 may determine whether the measurement of the first analyte (e.g., glucose) is limited due to the level of the second analyte (e.g., oxygen) based on whether a variance in the measurement of the first analyte during the trace is greater than a threshold. Detection of an oxygen limitation for a glucose sensor may be specific to a model of sensor. In an implementation, a machine-learning model may be trained to detect an oxygen limitation using a training set of glucose sensor traces labeled with corresponding oxygen sensor measurements. The model may output a measurement of variance such as a predicted error, which may then be compared to the threshold.

If the oxygen limitation is not detected, the glucose level may be used to infer a level of oxygen. For example, in block 520, the method 500 may include determining whether the glucose reading is above a threshold (e.g., 20 mg/dL). If the block 520 is true, in block 525, the estimation component 146 may estimate that the oxygen level is normal or high (e.g., above 80%). In block 530, the method 500 may include determining whether the glucose level is below a threshold (e.g., 15 mg/dL. If the block 530 is true, in block 535, the estimation component 146 may estimate that the oxygen level is very low (e.g., less than 90%).

Referring back to block 510, if the glucose trace shows an oxygen limitation, in block 540 the method 500 may include determining that the oxygen level is low and/or the glucose level is high (e.g., higher than indicated by the signal from the glucose sensor). In some implementations, a measurement by an oxygen sensor (e.g., sensor 120*b*) may be used to refine the interpretation of the glucose level. For instance, in block 550, the method 500 may include determining whether an oxygen reading is lower than a threshold (e.g., 80%). If the oxygen level is low, in block 570, the method may include confirming the oxygen level based on agreement between the glucose sensor and oxygen sensor. If the oxygen level is not low, in block 570, the method 500 may output a warning regarding the glucose level. For instance, the warning may indicate that an actual glucose level may be higher than indicated by the reading.

Figure 6:
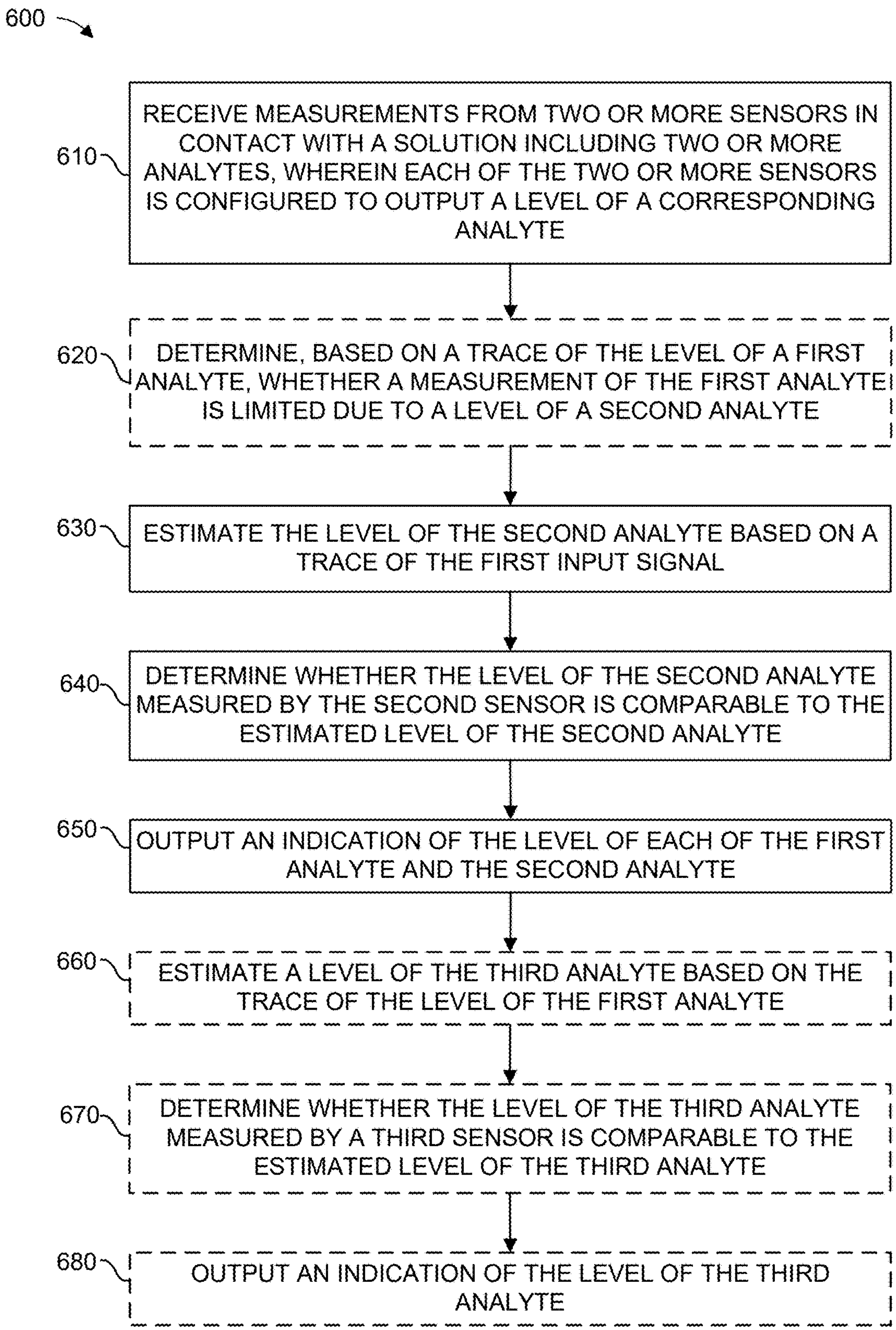
FIG. 6 is a flowchart of a method of operation of a multisensory device according to an aspect of the present disclosure.

FIG. 6 is a flowchart of a method 600 of operation of a multisensory system 100. The method 600 may be performed by the multisensory system 100 including the multisensory device 110, the analyzer 130, and the display 150.

In block 610, the method 600 includes receiving measurements from two or more sensors in contact with a solution including two or more analytes, wherein each of the two or more sensors is configured to output a level of a corresponding analyte. For example, the analyzer 130 may execute the input component 142 to receive measurements from two or more sensors 120 that are in contact with a solution (e.g., in channel 112) that includes two or more analytes. Each of the sensors 120 is configured to output a level of a corresponding analyte.

In block 620, the method 600 may optionally include, determining, based on a trace of the level of a first analyte, whether a measurement of the first analyte is limited due to a level of a second analyte. For example, the analyzer 130 may execute the limit detection component 144 to determine, based on the trace of the level of the first analyte, whether the measurement of the first analyte is limited due to the level of a second analyte. For example, the limit detection component 144 may perform the method 500 of FIG. 5. For example, as illustrated in block 510, the limit detection component 144 may determine that the measurement of the first analyte is limited due to the level of the second analyte when a variance in the measurement of the first analyte during the trace is greater than a threshold and determine that the measurement of the first analyte is not limited due to the level of the second analyte when the variance in the measurement of the first analyte during the trace is less than the threshold.

In block 630, the method 600 includes, estimating the level of the second analyte based on a trace of the first input signal. For example, the analyzer 130 may execute the limit detection component 144 and/or the estimation component 146 to estimate the level of the second analyte based on a trace (e.g., trace 210, 410, or 420) of the first input signal (e.g. from the first sensor 120*a*). For example, the estimation component 146 may perform the method 300 of FIG. 3 or the method 500 of FIG. 5.

In block 640, the method includes determining whether the level of the second analyte measured by the second sensor is comparable to the estimated level of the second analyte. For example, the analyzer 130 may execute the evaluation component 148 to determine whether the level of the second analyte measured by the second sensor (e.g., sensor 120*b* or sensor 120*c*) is comparable to the estimated level of the second analyte. In some implementations, where the estimated level of the second analyte is a range, the evaluation component 148 may determine whether the level of the second analyte measured by the second sensor is within the range of the estimated level. In other implementations, the evaluation component 148 may determine whether the level of the second analyte measured by the second sensor is within a threshold or margin of error of the estimated level.

In block 650, the method 600 includes outputting an indication of the level of each of the first analyte and the second analyte. For example, the analyzer 130 may execute the output component 149 to output the indication of the level of each of the first analyte and the second analyte to the display 150. In some implementations, the indication may also indicate whether the level of one or more of the analytes is confirmed by agreement with a second sensor.

In block 660, the method 600 may optionally include estimating a level of the third analyte based on the trace of the level of the first analyte. For example, the analyzer 130 may execute the estimation component 146 to estimate the level of the third analyte based on the trace of the level of the first analyte.

In block 670, the method 600 may optionally include determining whether the level of the third analyte measured by a third sensor is comparable to the estimated level of the third analyte. For example, the analyzer 130 may execute the evaluation component 148 to determine whether the level of the third analyte measured by a third sensor is comparable to the estimated level of the third analyte.

In block 680, the method 600 may optionally include outputting an indication of the level of the third analyte. For example, the analyzer 130 may execute the output component 149 to output the indication of the level of the third analyte to the display 150. In some implementations, the indication may also indicate whether the level of the third analyte is confirmed by agreement with the first sensor.

Example aspects are described in the following numbered clauses:

Clause 1. A method of analyzing a sample, comprising: receiving measurements from two or more sensors in contact with a solution including two or more analytes, wherein each of the two or more sensors is configured to output a level of a corresponding analyte; determining, based on a trace of the level of a first analyte, whether a measurement of the first analyte is limited due to a level of a second analyte; estimating a level of the second analyte based on whether the measurement of the first analyte is limited; determining whether the level of the second analyte measured by a second sensor is comparable to the estimated level of the second analyte; and outputting an indication of the level of each of the first analyte and the second analyte.

Clause 2. The method of clause 1, wherein the two or more sensors include a glucose sensor and an oxygen sensor.

Clause 3. The method of clause 1 or 2, wherein determining, based on the trace of the level of a first analyte, whether the measurement of the first analyte is limited due to a level of a second analyte comprises: determining that the measurement of the first analyte is limited due to the level of the second analyte when a variance in the measurement of the first analyte during the trace is greater than a threshold; and determining that the measurement of the first analyte is not limited due to the level of the second analyte when the variance in the measurement of the first analyte during the trace is less than the threshold.

Clause 4. The method of any of clauses 1-3, wherein estimating the level of the second analyte based on whether the measurement of the first analyte is limited comprises: estimating that the level of the first analyte is high or the level of the second analyte is low when the measurement of the first analyte is limited; estimating that the level of the second analyte is normal or high when the measurement of the first analyte is not limited and is above a first threshold level; and estimating that the level of the second analyte is extremely low when the level of the first analyte is below a second threshold level and the measurement of the first analyte is not limited.

Clause 5. The method of clause 4, further comprising outputting a warning that measurement of the first analyte is limited due to the level of the second analyte.

Clause 6. The method of any of clauses 1-5, further comprising: receiving a measurement from a third sensor in contact with the solution; estimating a level of a third analyte based on the trace of the level of the first analyte; determining whether the level of the third analyte measured by a third sensor is comparable to the estimated level of the third analyte; and outputting an indication of the level of the third analyte.

Clause 7. The method of clause 6, wherein the third sensor is one of a conductivity sensor configured to measure hematocrit (hct) or an optical sensor configured to measure hemoglobin (hb).

Clause 8. The method of clause 6 or 7, wherein estimating the level of a third analyte based on the trace of the level of the first analyte comprises: comparing the level of the first analyte during a sample to a baseline level of the first analyte after flushing the sample; estimating a high level of the third analyte when the baseline level of the first analyte after flushing the sample is greater than the level of the first analyte during the sample; estimating a low level of the third analyte when the baseline level of the first analyte after flushing the sample is less than the level of the first analyte during the sample; and estimating a normal level of the third analyte when the baseline level of the first analyte after flushing the sample is substantially equal to the level of the first analyte during the sample.

Clause 9. The method of any of clauses 6-8, further comprising determining a total ionic strength of the sample based on a difference between the level of the third analyte measured by the third sensor and the estimated level of the third analyte.

Clause 10. The method of clause 9, further comprising determining a total plasma protein level or a platelet level based on the total ionic strength and a sample conductivity.

Clause 11. A multisensory device, comprising: two or more sensors in contact with a channel, each sensor configured to output a corresponding level of an analyte in a sample in the channel; a memory storing computer-executable instructions; and one or more processors, individually or in combination, configured to: receive a first input signal from a first sensor of the two or more sensors indicating a level of a first analyte; receive a second input signal from a second sensor of the two or more sensors indicating a level of a second analyte; estimate the level of the second analyte based on a trace of the first input signal; and determine whether the level of the second analyte measured by the second sensor is comparable to the estimated level of the second analyte; and output an indication of the level of each of the first analyte and the second analyte.

Clause 12. The multisensory device of clause 11, further comprising: a third sensor in contact with the channel and configured to output third signal indicating a level of a third analyte in the sample in the channel, wherein the one or more processors, individually or in combination, are configured to: estimate a level of the third analyte based on the trace of the level of the first analyte; determine whether the level of the third analyte measured by a third sensor is comparable to the estimated level of the third analyte; and output an indication of the level of the third analyte.

Clause 13. The multisensory device of clause 11 or 12, wherein the first sensor is a glucose sensor and the second sensor is one of: an oxygen sensor configured to measure oxygen, a conductivity sensor configured to measure hematocrit (hct), or an optical sensor configured to measure hemoglobin (hb).

Clause 14. The multisensory device of any of clauses 11-13, wherein to estimate the level of the second analyte based on the trace of the first input signal, the one or more processors, individually or in combination, are configured to: determine, based on the trace of the level of the first analyte, whether a measurement of the first analyte is limited due to the level of a second analyte; and estimate the level of the second analyte based on whether the measurement of the first analyte is limited.

Clause 15. The multisensory device of clause 14, wherein to estimate the level of the second analyte based on whether the measurement of the first analyte is limited, the one or more processors, individually or in combination are configured to: estimate that the level of the first analyte is high or the level of the second analyte is low when the measurement of the first analyte is limited; estimate that the level of the second analyte is normal or high when the measurement of the first analyte is not limited and is above a first threshold level; and estimate that the level of the second analyte is extremely low when the level of the first analyte is below a second threshold level and the measurement of the first analyte is not limited.

Clause 16. The multisensory device of clause 14 or 15, wherein to determine, based on the trace of the level of the first analyte, whether the measurement of the first analyte is limited due to a level of a second, the one or more processors, individually or in combination, are configured to: determine that the measurement of the first analyte is limited due to the level of the second analyte when a variance in the measurement of the first analyte during the trace is greater than a threshold; and determine that the measurement of the first analyte is not limited due to the level of the second analyte when the variance in the measurement of the first analyte during the trace is less than the threshold.

Clause 17. The multisensory device of any of clauses 14-16, wherein the one or more processors, individually or in combination, are configured to output a warning that measurement of the first analyte is limited due to the level of the second analyte.

Clause 18. The multisensory device of any of clauses 11-17, wherein to estimate the level of the second analyte based on a trace of the first input signal, the one or more processors, individually or in combination, are configured to: compare the level of the first analyte during a sample to a baseline level of the first analyte after flushing the sample; estimate a high level of the second analyte when the baseline level of the first analyte after flushing the sample is greater than the level of the first analyte during the sample; estimate a low level of the second analyte when the baseline level of the first analyte after flushing the sample is less than the level of the first analyte during the sample; and estimating a normal level of the second analyte when the baseline level of the first analyte after flushing the sample is substantially equal to the level of the first analyte during the sample.

Clause 19. The multisensory device of any of clauses 11-18, wherein the one or more processors, individually or in combination, are configured to determine a total ionic strength of the sample based on a difference between the level of the second analyte measured by the second sensor and the estimated level of the second analyte.

Clause 20. The multisensory device of clause 19, wherein the one or more processors, individually or in combination, are configured to determine a total plasma protein level or a platelet level based on the total ionic strength and a sample conductivity.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of any device as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

The invention claimed is:

1. A method of analyzing a sample by a multisensory device, comprising:

receiving, at a processor of the multisensory device, measurements from two or more electrochemical sensors of the multisensory device in contact with a solution including two or more analytes, wherein each of the two or more electrochemical sensors is configured to output a level of a corresponding analyte;

determining, by the processor, based on a trace of the level of a first analyte, whether a measurement of the first analyte is limited due to a level of a second analyte;

estimating, by the processor, a level of the second analyte based on whether the measurement of the first analyte is limited;

determining, by the processor, whether the level of the second analyte measured by a second electrochemical sensor is comparable to the estimated level of the second analyte;

outputting, from the multisensory device, an indication of the level of each of the first analyte and the second analyte; and outputting, from the multisensory device, a warning that the measurement of the first analyte is limited due to the level of the second analyte.

2. The method of claim 1, wherein the two or more electrochemical sensors include a glucose sensor and an oxygen sensor.

3. The method of claim 1, wherein determining, based on the trace of the level of a first analyte, whether the measurement of the first analyte is limited due to a level of a second analyte comprises:

determining that the measurement of the first analyte is limited due to the level of the second analyte when a variance in the measurement of the first analyte during the trace is greater than a threshold; and determining that the measurement of the first analyte is not limited due to the level of the second analyte when the variance in the measurement of the first analyte during the trace is less than the threshold.

4. The method of claim 1, wherein estimating the level of the second analyte based on whether the measurement of the first analyte is limited comprises:

estimating that the level of the first analyte is high or the level of the second analyte is low when the measurement of the first analyte is limited;

estimating that the level of the second analyte is normal or high when the measurement of the first analyte is not limited and is above a first threshold level; and estimating that the level of the second analyte is extremely low when the level of the first analyte is below a second threshold level and the measurement of the first analyte is not limited.

5. The method of claim 4, wherein the warning indicates that measurement of the first analyte is limited due to the level of the second analyte in response to the level of the second analyte measured by a second electrochemical sensor not being comparable to the estimated level of the second analyte.

6. The method of claim 1, further comprising:

receiving a measurement from a third electrochemical sensor in contact with the solution;

estimating a level of a third analyte based on the trace of the level of the first analyte;

determining whether the level of the third analyte measured by the third sensor is comparable to the estimated level of the third analyte; and outputting an indication of the level of the third analyte.

7. The method of claim 6, wherein the third sensor is one of a conductivity sensor configured to measure hematocrit (hct) or an optical sensor configured to measure hemoglobin (hb).

8. The method of claim 6, wherein estimating the level of a third analyte based on the trace of the level of the first analyte comprises:

comparing the level of the first analyte during a sample to a baseline level of the first analyte after flushing the sample;

estimating a high level of the third analyte when the baseline level of the first analyte after flushing the sample is greater than the level of the first analyte during the sample;

estimating a low level of the third analyte when the baseline level of the first analyte after flushing the sample is less than the level of the first analyte during the sample; and estimating a normal level of the third analyte when the baseline level of the first analyte after flushing the sample is substantially equal to the level of the first analyte during the sample.

9. The method of claim 6, further comprising determining a total ionic strength of the sample based on a difference between the level of the third analyte measured by the third sensor and the estimated level of the third analyte.

10. The method of claim 9, further comprising determining a total plasma protein level or a platelet level based on the total ionic strength and a sample conductivity.

11. A multisensory device, comprising:

two or more electrochemical sensors in contact with a channel, each electrochemical sensor configured to output a corresponding level of an analyte in a sample in the channel;

a memory storing computer-executable instructions; and one or more processors, individually or in combination, configured to:

receive a first input signal from a first sensor of the two or more electrochemical sensors indicating a level of a first analyte;

receive a second input signal from a second sensor of the two or more electrochemical sensors indicating a level of a second analyte;

estimate the level of the second analyte based on a trace of the first input signal; and determine whether the level of the second analyte measured by the second sensor is comparable to the estimated level of the second analyte;

output an indication of the level of each of the first analyte and the second analyte; and output a warning that the measurement of the first analyte is limited due to the level of the second analyte.

12. The multisensory device of claim 11, further comprising:

a third sensor in contact with the channel and configured to output third signal indicating a level of a third analyte in the sample in the channel, wherein the one or more processors, individually or in combination, are configured to:

estimate a level of the third analyte based on the trace of the level of the first analyte;

determine whether the level of the third analyte measured by a third sensor is comparable to the estimated level of the third analyte; and output an indication of the level of the third analyte.

13. The multisensory device of claim 11, wherein the first sensor is a glucose sensor and the second sensor is one of: an oxygen sensor configured to measure oxygen, a conductivity sensor configured to measure hematocrit (hct), or an optical sensor configured to measure hemoglobin (hb).

14. The multisensory device of claim 11, wherein to estimate the level of the second analyte based on the trace of the first input signal, the one or more processors, individually or in combination, are configured to:

determine, based on the trace of the level of the first analyte, whether a measurement of the first analyte is limited due to the level of a second analyte; and estimate the level of the second analyte based on whether the measurement of the first analyte is limited.

15. The multisensory device of claim 14, wherein to estimate the level of the second analyte based on whether the measurement of the first analyte is limited, the one or more processors, individually or in combination are configured to:

estimate that the level of the first analyte is high or the level of the second analyte is low when the measurement of the first analyte is limited;

estimate that the level of the second analyte is normal or high when the measurement of the first analyte is not limited and is above a first threshold level; and estimate that the level of the second analyte is extremely low when the level of the first analyte is below a second threshold level and the measurement of the first analyte is not limited.

16. The multisensory device of claim 14, wherein to determine, based on the trace of the level of the first analyte, whether the measurement of the first analyte is limited due to a level of a second, the one or more processors, individually or in combination, are configured to:

determine that the measurement of the first analyte is limited due to the level of the second analyte when a variance in the measurement of the first analyte during the trace is greater than a threshold; and determine that the measurement of the first analyte is not limited due to the level of the second analyte when the variance in the measurement of the first analyte during the trace is less than the threshold.

17. The multisensory device of claim 14, wherein the one or more processors, individually or in combination, are configured to output the warning that measurement of the first analyte is limited due to the level of the second analyte in response to the level of the second analyte measured by the second sensor not being comparable to the estimated level of the second analyte.

18. The multisensory device of claim 11, wherein to estimate the level of the second analyte based on a trace of the first input signal, the one or more processors, individually or in combination, are configured to:

compare the level of the first analyte during a sample to a baseline level of the first analyte after flushing the sample;

estimate a high level of the second analyte when the baseline level of the first analyte after flushing the sample is greater than the level of the first analyte during the sample;

estimate a low level of the second analyte when the baseline level of the first analyte after flushing the sample is less than the level of the first analyte during the sample; and estimating a normal level of the second analyte when the baseline level of the first analyte after flushing the sample is substantially equal to the level of the first analyte during the sample.

19. The multisensory device of claim 11, wherein the one or more processors, individually or in combination, are configured to determine a total ionic strength of the sample based on a difference between the level of the second analyte measured by the second sensor and the estimated level of the second analyte.

20. The multisensory device of claim 19, wherein the one or more processors, individually or in combination, are configured to determine a total plasma protein level or a platelet level based on the total ionic strength and a sample conductivity.

* * * * *